(12) United States Patent
Onishi et al.

(10) Patent No.: US 7,555,952 B2
(45) Date of Patent: Jul. 7, 2009

(54) SENSING DEVICE

(75) Inventors: Naoki Onishi, Sayama (JP); Tsuyoshi Shiobara, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 44 days.

(21) Appl. No.: 11/793,985

(22) PCT Filed: Dec. 28, 2005

(86) PCT No.: PCT/JP2005/024272

§ 371 (c)(1),
(2), (4) Date: Aug. 27, 2007

(87) PCT Pub. No.: WO2006/070940

PCT Pub. Date: Jul. 6, 2006

(65) Prior Publication Data

US 2008/0156097 A1    Jul. 3, 2008

(30) Foreign Application Priority Data

Dec. 28, 2004  (JP) .............................. 2004-381432

(51) Int. Cl.
    G01H 1/00   (2006.01)
    G01L 1/00   (2006.01)
    G01N 21/00  (2006.01)

(52) U.S. Cl. ................. 73/579; 73/61.49; 73/64.53; 310/323.21

(58) Field of Classification Search .................. 73/579, 73/570, 582, 590, 61.49, 61.79, 64.53; 310/319, 310/323.21
    See application file for complete search history.

(56) References Cited

U.S. PATENT DOCUMENTS

| 4,991,283 | A | 2/1991 | Johnson et al. |
|---|---|---|---|
| 5,196,347 | A | 3/1993 | Kaneko et al. |
| 5,494,639 | A | 2/1996 | Grzegorzewski |
| 5,892,143 | A | 4/1999 | Namerikawa et al. |
| 6,210,226 | B1 | 4/2001 | Zhu et al. |
| 6,321,588 | B1 * | 11/2001 | Bowers et al. ............. 73/24.01 |
| 6,525,549 | B1 | 2/2003 | Poellmann |
| 6,938,462 | B2 | 9/2005 | Jakoby et al. |
| 7,055,377 | B2 | 6/2006 | Paul et al. |
| 7,331,232 | B2 * | 2/2008 | Itoh et al. ..................... 73/590 |
| 2004/0016297 | A1 | 1/2004 | Paul et al. |

(Continued)

FOREIGN PATENT DOCUMENTS

JP          1-244335         9/1989

(Continued)

Primary Examiner—Hezron Williams
Assistant Examiner—Samir M Shah
(74) Attorney, Agent, or Firm—Jordan and Hamburg LLP

(57) ABSTRACT

The present invention prevents instability of frequency measurement caused by spatial connection between quartz sensors adjacent to each other when a plurality of quartz sensors, including a quartz resonator which varies a national frequency due to adsorption of an object, are to be detected. A common measuring unit measures a variation in frequency of each oscillation circuit corresponding to each quartz sensor by switching and connection in turn, and the oscillation circuits, excepting an oscillation circuit connected to the measuring unit by switches, are connected to a load on the output side of the oscillation circuit channels connected to the measuring unit and the load value is such that the respective oscillating frequencies are forcibly separated from each other.

18 Claims, 8 Drawing Sheets

U.S. PATENT DOCUMENTS

| | | | |
|---|---|---|---|
| 2004/0187580 A1* | 9/2004 | Nozaki | 73/580 |
| 2005/0052813 A1 | 3/2005 | Kobayashi | |
| 2005/0069864 A1* | 3/2005 | Itoh et al. | 435/4 |
| 2006/0141608 A1 | 6/2006 | Aastrup et al. | |
| 2008/0047331 A1* | 2/2008 | Wakamatsu et al. | 73/61.79 |
| 2008/0129148 A1* | 6/2008 | Wakamatsu et al. | 310/319 |
| 2008/0134767 A1* | 6/2008 | Wakamatsu et al. | 73/61.79 |
| 2008/0156097 A1 | 7/2008 | Onishi et al. | |

FOREIGN PATENT DOCUMENTS

| | | |
|---|---|---|
| JP | 3-257346 | 11/1991 |
| JP | 4-1554 | 1/1992 |
| JP | 4-9744 | 1/1992 |
| JP | 5-5735 | 1/1993 |
| JP | 7-190916 | 7/1995 |
| JP | 9-145583 | 6/1997 |
| JP | 9-250936 | 9/1997 |
| JP | 10-142134 | 5/1998 |
| JP | 10-332463 | 12/1998 |
| JP | 11-183479 | 7/1999 |
| JP | 2000-338022 | 12/2000 |
| JP | 2001-83154 | 3/2001 |
| JP | 2001-099777 | 4/2001 |
| JP | 2001-201436 | 7/2001 |
| JP | 2002-148295 | 5/2002 |
| JP | 2002148295 A * | 5/2002 |
| JP | 2002-243607 | 8/2002 |
| JP | 2002-525578 | 8/2002 |
| JP | 2004-205392 | 7/2004 |
| JP | 2004-264254 | 9/2004 |
| JP | 2004-317493 | 11/2004 |
| JP | 2004-340766 | 12/2004 |
| JP | 2005-413123 | 2/2005 |

* cited by examiner

SENSING DEVICE

DESCRIPTION

1. Technical Field

The present invention relates to a sensing device that uses a resonator, e.g. a quartz resonator, which has an adsorbing layer for adsorbing an object to be detected on the surface of the resonator and changes the natural frequency thereof by adsorbing of the object, and senses the objects by detecting the variation in the natural frequency of the sensor resonator.

2. Background Art

The necessity to know the concentration of various pollutants in a river or soil has been increasing for the purpose of maintaining environmental preservation. There are some pollutants which have very strong toxicity to the human body even with a very small quantity. Consequently, the establishment of measurement technology for the pollutants in a very small quantity has been expected. Dioxin is one of the pollutants on which much attention has been recently focused and methods of using a gas chromatography mass spectrometer and Enzyme-Linked Immuno Sorbent Assay (ELISA) are known as a method of measuring dioxin. Although it is possible to perform highly accurate microanalysis of the order of $10^{-22}$ g/ml by gas chromatography mass spectrometry, the method has disadvantages in that the measurement device is very costly, which makes the case of analysis unexpectedly expensive, and furthermore, it takes a long time for results to be known. In the meantime, the ELISA method is cheaper in price for the equipment and analysis, and less time consuming, compared with the gas chromatography mass spectrometry, but it has the disadvantage of low accuracy of the order of $10^{-9}$ g/ml.

Consequently, the present inventor pays attention to a quartz sensor which uses a quartz resonator as a measurement device for pollutants such as dioxin because once an object to be detected adheres to the quartz resonator, the natural frequency thereof varies according to the amount of adhesion. Recently, the development of antibodies that chemically bond with only certain specific molecules has become popular, and it has become possible to perform analysis in various fields by forming an adsorbing layer using an antibody that causes an antibody-antigenic reaction against a sample on the surface of the quartz resonator (or to be more exact, on the electrode surface) in advance.

Meanwhile, in a method to measure a pollutant in a solution or an antibody in blood using a quartz resonator, cleaning is necessary for repeated use of a sensor portion, it sometimes takes a long time for the antibody-antigenic reaction, and furthermore, a static evaluation is conducted by obtaining distribution data through measurement of many samples. Therefore, an efficient method is desired. Under these circumstances, the present inventor attempts to measure simultaneously using many quartz sensors. The technology of using many quartz sensors is described in Japanese Patent Application Laid Open No. 2001-99777: FIGS. 1 and 24 which discloses technology to measure the type of corrosive substances in the air and the concentration thereof.

When measurement is conducted using many quartz sensors, there exists the following disadvantage. That is, although the oscillation frequency of a quartz resonator is determined by the design value, it is practically impossible for actual products to make each oscillation frequency precisely identical to one another. It is also practically impossible to form adsorbing layers with absolutely the same size and thickness on the electrode surfaces. Therefore, there is a frequency difference between each though very small. Accordingly, when a distance between respective quartz sensors is small, in other words, when the distance between the quartz sensors adjacent each other is small, these quartz sensors are spatially connected so that the oscillation frequencies become unstable affected by mutual frequencies. This phenomenon resembles that when antennas are brought closer together, the oscillation frequency becomes unstable, which makes it impossible to measure the frequency accurately. Therefore, it becomes difficult to detect an object, in other words, it becomes difficult to measure an exact concentration of the object or to detect presence or absence of the object in very small quantities with a high degree of accuracy. FIG. 11 shows an example of the situations that between quartz sensors which are close to each other, one spectrum relating to the measurement overlaps with the other spectrum relating to the measurement.

Though it is possible to avoid such phenomena by making the distance between respective quartz sensors greater, this can result in the device being too large. The present inventor is attempting to measure the concentration of an object, for instance, in 8 sample solutions prepared by diluting the sample solution containing the object with eight different degrees of dilution, using eight quartz sensors having the same oscillation frequency design value, and evaluating their concentration statistically. When a large number of the quartz sensors are used, the device cannot be minimized sufficiently and it departs from the market demand unless they are arranged in a closely packed fashion.

DISCLOSURE OF THE INVENTION

The present invention has been achieved under such a circumstance, and an object of the present invention is to provide a technology to conduct detection of an object to be detected (measurement of concentration or detection of the presence or absence of the object to be detected) in a stable fashion in a sensing device using a plurality of sensor resonators including a piezoelectric plate, such as a quartz board, which forms an adsorbing layer to adsorb an object to be detected on a surface thereof and which changes a natural frequency thereof by adsorption of the object.

The sensing device of the present invention uses a sensor resonator including a piezoelectric plate forming an adsorbing layer to adsorb an object to be detected on the surface thereof and change the natural frequency thereof by adsorption of the object, and detects the object by variation of the natural frequency of the sensor resonator. The present invention comprises:

a plurality of sensor resonators;

a plurality of the oscillation circuits to oscillate the plurality of the sensor resonators respectively;

a measuring unit provided for the plural oscillation circuits in common to measure a signal relating a frequency of the oscillation circuit;

a signal switchover unit to perform switchover connection of the plural oscillation circuits to the measuring unit in turn;

a load switchover unit installed between each of the plural oscillation circuits and the signal switchover unit to switchover the load on the output side of each oscillation circuit between a first value and a second value in order to forcibly separate the respective oscillation frequencies of the oscillation circuits connected to the measuring unit from the oscillation circuit not connected to the measuring unit; and a switchover controller which outputs a control signal to the signal switchover unit so that each of the plural oscillation circuits is connected to the measuring unit in turn, and outputs a control signal to the load switchover unit so that the load on the output side of the oscillation circuit connected to the measuring unit is the first value and the load on the output side of the oscillation circuit selected from among the oscillation circuits not connected to the measuring unit is the second value.

The load switchover unit includes: for instance, a plurality of terminal loads having the second values respectively provided at the terminals of the plural oscillation circuits; and a switch provided between each of the plural oscillation circuits and the signal switchover units to switchover and connect the output side of each oscillation circuit between the signal switchover unit and the terminal load having the second value, and the switchover controller outputs a control signal to the switch so that the oscillation circuits selected from among the oscillation circuits not connected to the measuring unit respectively connect to the terminal load. More concretely, it is possible to cite a formation in that buffer circuits are provided between the respective oscillation circuits and the signal switchover units and the switch is provided between each oscillation circuit and each buffer circuit. The oscillation circuits selected from among the oscillation circuits not connected to the measuring unit can be all of the oscillation circuits not connected to the measuring unit or can be a part of the oscillation circuits. The sensing device of the present invention includes a sensor unit including a holding member provided on every sensor resonator to hold each sensor resonator and connection terminals of the sensor resonator electrodes; and a measuring device main unit, detachably provided to the connection terminal of the sensor unit and at the same time includes each oscillation circuit and the measuring unit.

According to the present invention, when a plurality of sensor resonators, for instance, quartz resonators of which natural frequency changes due to adsorption of an object to be detected, a common measuring unit to measure the change of the frequency is provided for each oscillation circuit corresponding to each sensor resonator so as to perform switchover connection in turn, and is structured in a manner that the terminal loads of the oscillation circuit connected to the measuring unit are the first values, and the terminal loads of the oscillation circuits selected from among the oscillation circuit not connected to the measuring unit, for instance, the terminal loads of all oscillation circuits not connected to the measuring unit are the second values. Therefore, it is possible to avoid overlapping of mutual spectrum by forcibly separating the mutual oscillation frequencies of the sensor resonator from each other. Accordingly, it is possible to perform detection of the object (measurement of concentration and measurement of the presence or absence of the object to be detected) in a stable fashion. Furthermore, since the measuring unit is used in common for a plurality of sensor resonators, the circuit configuration is simple, so that the cost reduction can be realized.

BEST MODE FOR CARRYING OUT THE INVENTION

Figure 1:
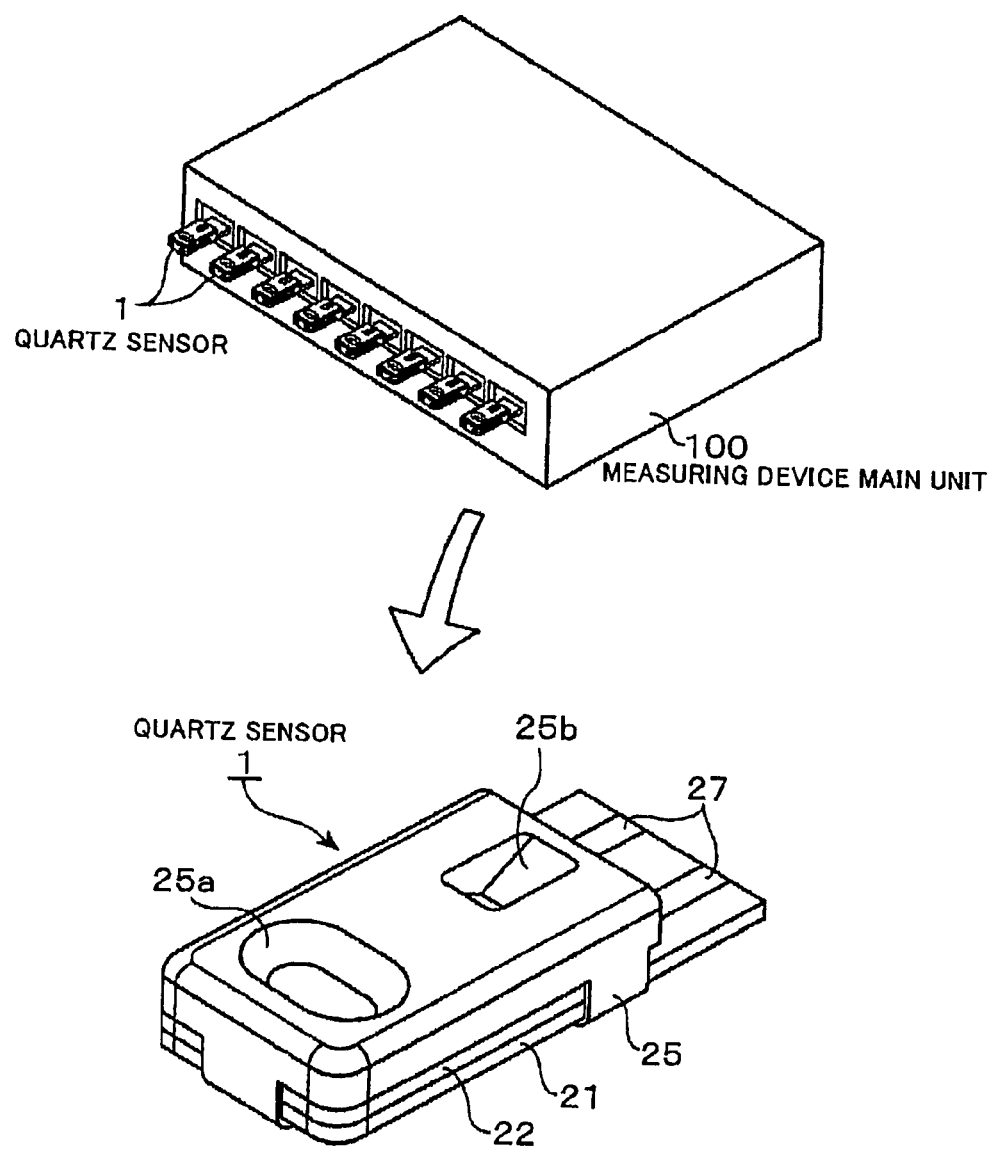
FIG. 1 is a perspective view showing an outside appearance of an embodiment of the sensing device and a quartz sensor relating to the present invention.
Figure 2:
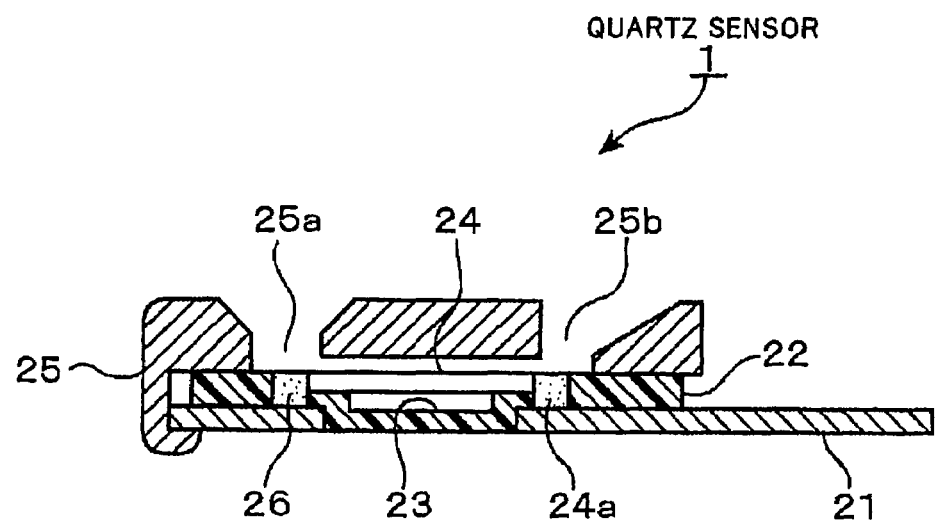
FIG. 2 is a vertical cross section showing the quartz sensor used in the above-described embodiment.

Hereinafter, an embodiment of a sensing device relating to the present invention will be explained. Though the present embodiment has a principal portion in a rear circuit part of an oscillation circuit, a whole structure will be explained briefly first. The sensing device includes a quartz sensor 1 composed of a plurality of, for instance 8 sensor units; and a measurement device main unit 100 to which the quartz sensor 1 is detachably installed, as shown in FIG. 1. As shown in FIG. 1 and FIG. 2, the quartz sensor 1 is structured in a manner that a rubber sheet 22 is placed upon a printed circuit board 21 which is a wiring board, a quartz resonator 24 is placed to cover a recess 23 arranged in the rubber sheet 22, and an upper lid case 25 is mounted on the rubber sheet 22. The printed circuit board 21 and the rubber sheet 22 serve as a holding member, and the quartz resonator 24 corresponds to a sensor resonator. A pouring opening 25a for a sample solution and an observation opening 25b of the sample solution are formed in the upper lid case 25, and the sample solution is poured in from the pouring opening 25, so that the space on the upper surface side of the quartz resonator 24 is filled with the sample solution. An airtight space is formed by the recess 23 on the lower surface side of the quartz resonator 24, thereby composing a Langevin type quartz sensor.

Figure 3:
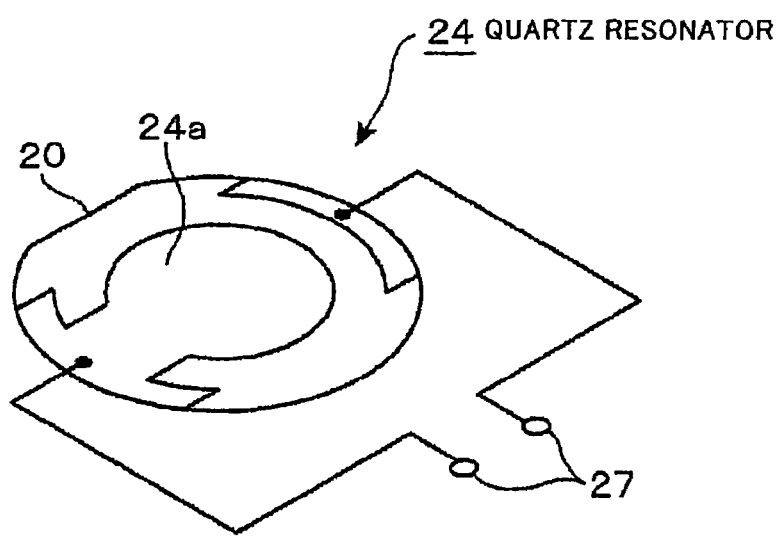
FIG. 3 is a perspective view showing a quartz resonator and a connection terminal used for the quartz sensor.

The quartz resonator 24 includes electrodes 24a and 24a (electrodes on the back surface side cannot be seen) on both surfaces of, for instance a round shaped, quartz plate 20 as shown in FIG. 3, and these electrodes 24a and 24a are electrically connected to a connection terminal 27 attached to the printed circuit board 21 via a conductive adhesive 26. An adsorbing layer (not shown) for adsorbing an object to be detected is formed on one surface of the quartz resonator 24, for instance, on the surface of the electrode 24a. The connection terminals 27 of the respective quartz sensors 1 are detachably fixed directly on the connection terminal side of the measuring device main unit 100. When the connection terminals 27 are connected, the respective quartz sensors 1 are arranged in a horizontal line and the pouring openings 25a face upward. In this embodiment, the quartz plate 20 corresponds to a piezoelectric plate which changes natural frequency by adsorption of the object.

Figure 4:
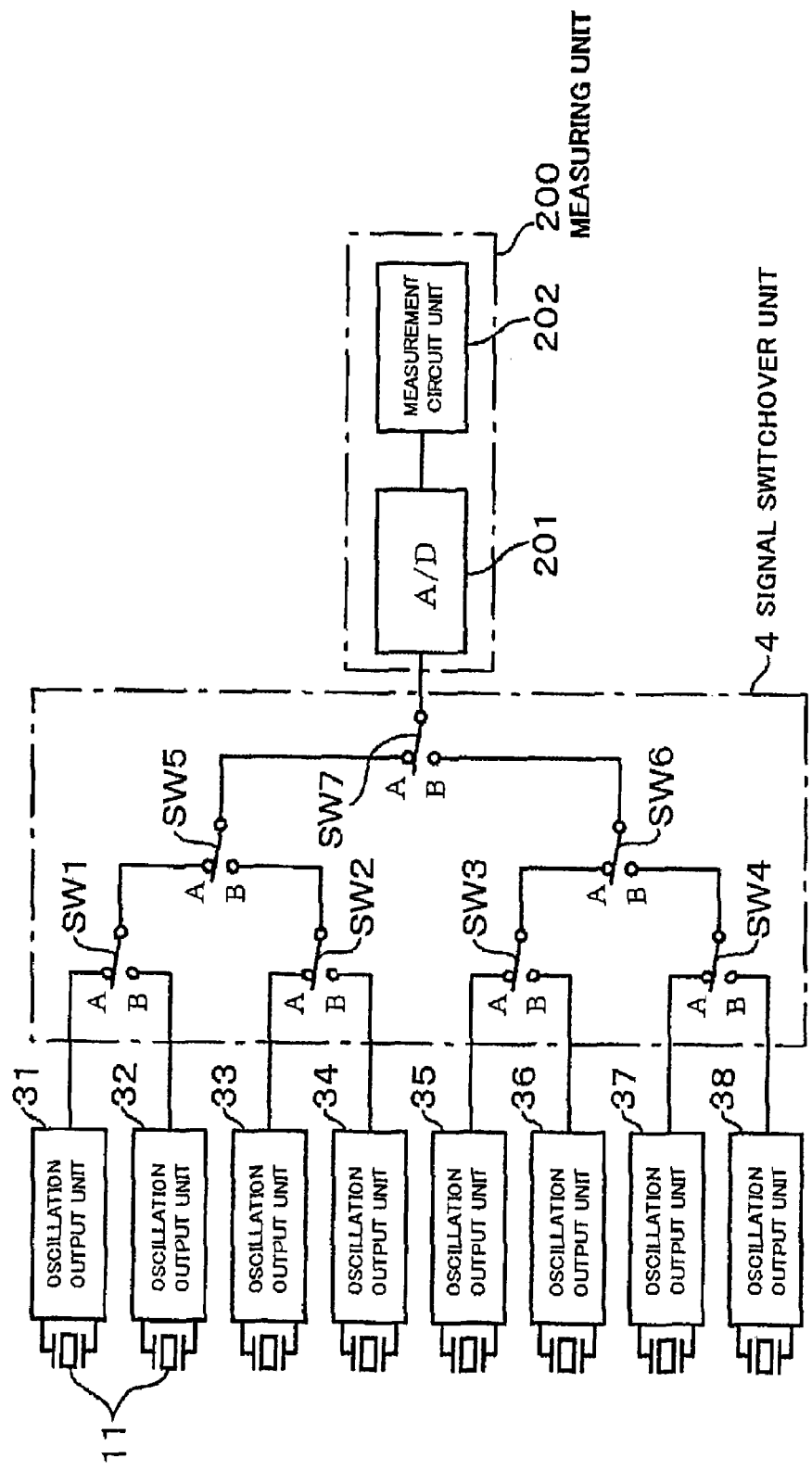
FIG. 4 is a block diagram showing a whole circuit configuration of the above embodiment.

The measuring device main unit 100 includes an oscillation circuit for oscillating the quartz sensor 1 and a measuring unit for measuring a frequency of a frequency signal from the oscillation circuit. An inner circuit of the measuring device main unit 100 will be explained in reference to FIG. 4. In this embodiment, oscillation output units are provided in 8 channels so as to install 8 quartz sensors 1. These oscillation circuits in 8 channels are shown by the number 31 to 38. A measuring unit 200 for measuring signals relating the frequency of the oscillation circuit is connected to a rear part of the oscillation output units 31 to 38 via a signal switchover unit 4. The signal switchover unit 4 is structured such that anyone of the oscillation output units 31 to 38, in other words, one of 8 channels on the detection terminal side is connected to the measuring unit 200 by combining the switches SW1 to SW7.

The measuring unit 200 may be a means for measuring the frequency of, for instance, the oscillation circuit and determine a deviation based on the measurement, but may be a means for directly determining a deviation in frequency of the oscillation circuit as will be described later. In this embodiment, the measuring unit 200 includes an analog/digital (A/D) converter 201 which converts a frequency signal (analogue signal) sent from anyone of the oscillation output units 31 to 38 into a digital signal and a measurement circuit unit 202 for measuring the frequency or directly measuring the deviation in frequency by processing the digital signal from the A/D converter 201.

Figure 5:
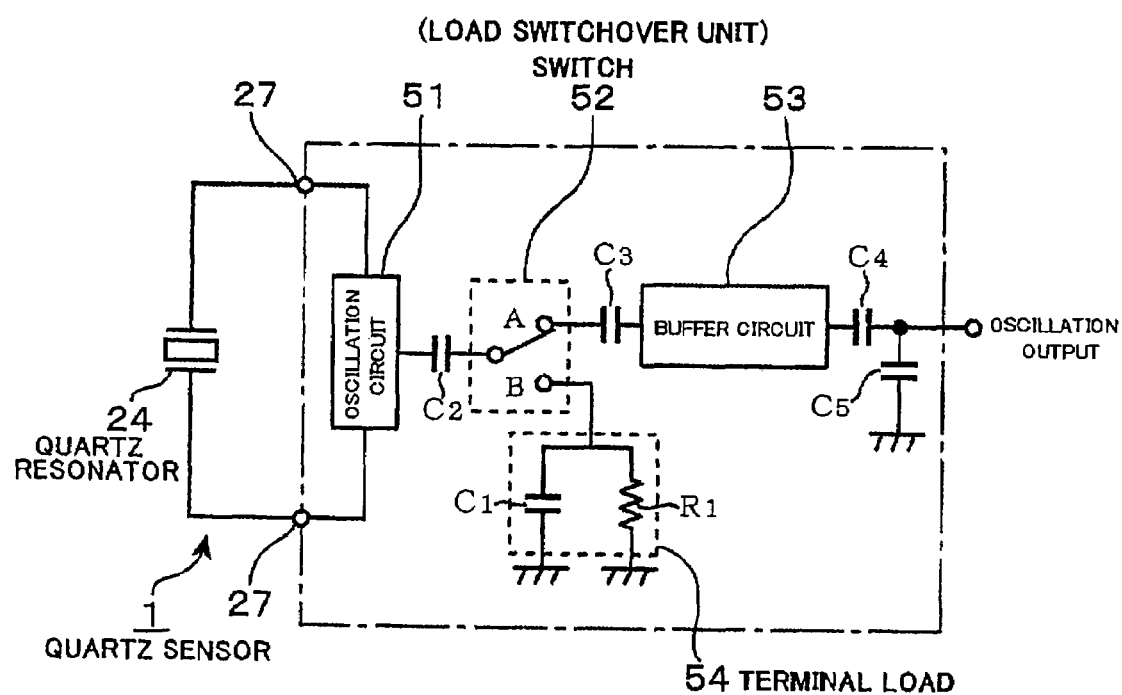
FIG. 5 is a circuit diagram showing an oscillation output unit used for the circuit of the above embodiment.

A structure of the oscillation output unit 31, representing the oscillation output units 31 to 38, will be explained in reference to FIG. 5. The oscillation output unit 31 includes: an oscillation circuit 51 of oscillating the quartz resonator 24, composed of, for instance, a Colpitts circuit; a switch 52 serving as a load switchover unit connected to the output side of the oscillation circuit 51, a buffer circuit 53 connected to the switchover contact point A side of the switch 52, and a terminal load 54 connected to the other switchover contact point B side and composed of, for instance, a parallel circuit of a capacitor C1 and a resistor R1. C2 to C5 are capacitors.

Since the oscillation frequency and the output level are influenced by the load value on the output side, the oscillation circuit 51 is connected to the measuring unit 200 via the buffer circuit 53 lest the load value should fluctuate. The present invention utilizes that the oscillation frequency and the output level of the oscillation circuit 51 changes according to a magnitude of the load on the output side as described above, and when the oscillation circuit 51 is not connected to the measuring unit 200, the output side of the oscillation circuit 51 is connected to the terminal load 54 by switchover of the switch 52, so as to be an oscillation frequency different from the oscillation frequency which is obtained when connected to the buffer circuit 53. That is, assuming that the load on the output side is a first value when the oscillation circuit 51 is connected to the buffer circuit 53, the load on the output side is a second value when it is switch over onto the terminal load 54 side. The second value is set to be a size that can avoid overlapping of mutual spectrums by forcibly separating the oscillation frequency of the oscillation circuit 51 in the channels connected to the measuring unit 200, among 8, channels from the oscillation frequency of the oscillation circuit 51 in the channels not connected to the measuring unit 200. In addition, the absolute amount of connection itself is also reduced by making the output level lower. More specifically, for instance, the value (the second value) of the terminal load 54 is set such that the oscillation frequency at the time when the switch 52 is switched over on the terminal load 54 side is shifted about several hundred ppm with regard to the oscillation frequency at the time when the switch 52 is switched over on the buffer circuit 53 side. Far more specifically, for instance, in the case of oscillation circuit of 31.1 MHz, it is set so as to be displaced by 25 kHz.

As described above, in order to avoid overlapping of spectrum for the output of mutual oscillation circuits 51, in other words, in order to avoid the phenomenon that the oscillation frequency becomes unstable influenced by mutual oscillation frequency, it is preferable that the displacement of oscillation frequency is as large as possible. However, if it is made too large, it takes a long time until the oscillation frequency returns to the original magnitude and gets stable when the channel switched off from the measuring unit 200 is connected to the measuring unit 200. Then, the channel switchover speed is reduced, which requires a long time for the measurement. Therefore, the amount of displacement is determined considering both situations.

Figure 6:
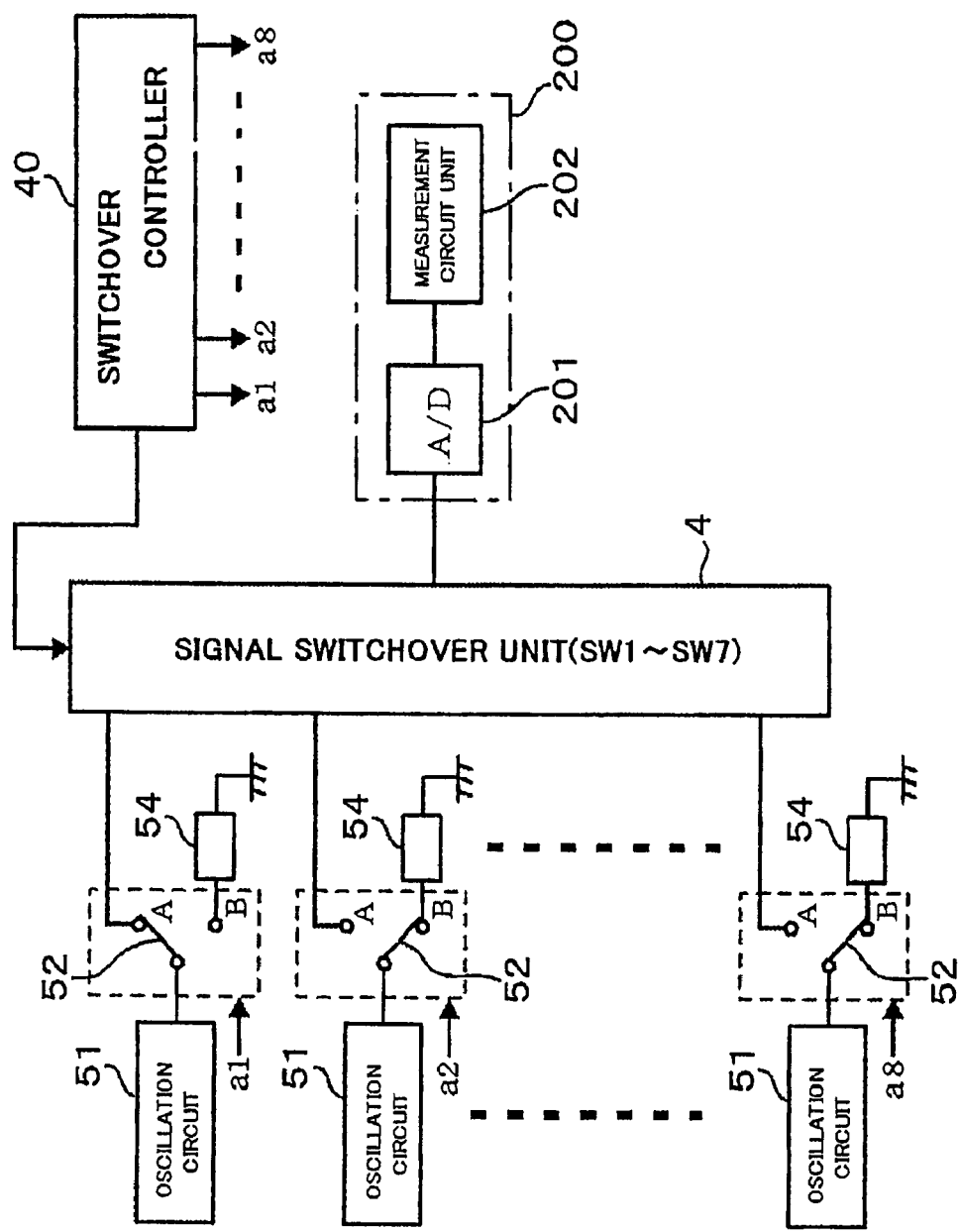
FIG. 6 is a block circuit diagram showing a simplified whole circuit and a state of switchover of a terminal load switchover unit of the above embodiment.

FIG. 6 is a circuit diagram showing the oscillation circuit 51, the switch 52 serving as a load switchover unit and the switchover controller 40 in linking together in the respective 8 channels. The switchover controller 40 has a function to output a control signal to the signal switchover unit 4 so that each of the oscillation circuits 51 is connected to the measuring unit 200 one by one in turn, in other words, so that each of the eight channels comes to be in a state of being connected one by one in turn, and to output a control signal to the switch 52 so as to connect to the terminal loads 54 respectively as for the oscillation circuits except the oscillation circuits 51 in the channels connected to the measuring unit 200.

Next, the function of the above embodiment will be explained. First, the quartz sensor 1 is plugged into the measuring device main unit 100, and the respective channels including the oscillation circuits 51 are connected to the measuring unit 200 by the signal switchover unit 4 in turn, for instance, in a state that the quartz sensor 1 is not filled. In the measuring unit 200, the oscillation frequency from each oscillation circuit 51 is taken in the measurement circuit unit 202 via the A/D converter 201 to determine each oscillation frequency (blank value) at this time, for instance. Note that in order to determine the blank value, pure water or other solutions may have been poured into the quartz sensor 1. Then, 8 kinds of the sample solution for measurement are prepared by changing the dilution ratio of the sample solution to be measured, which are poured into 8 quartz sensors 1. Each channel is connected to the measuring unit 200 by the signal switchover unit 4 in turn to find each oscillation frequency, had the deviation in the oscillation frequency caused by pouring the sample solutions for each channel are determined. It should be noted that in this case, the deviation caused by coming into contact of the quartz resonator 24 with the liquid is included in addition to that caused by adsorption of the object onto the adsorbing layer of the quartz resonator 24. Therefore, it is possible to perform the measurement in such a manner that the amount of deviation in oscillation frequency is determined in advance at the time of pouring, for instance, pure water into the quartz sensor 1 and the value obtained by canceling the amount of deviation is handled as the measurement value for the variation in frequency. It is also possible to conduct the measurement operation in such a manner that the oscillation frequency is measured after pouring pure water and before pouring the sample solution into the quartz sensor 1 and then the sample solution is poured into the quartz sensor 1 instead of pure water.

Synchronizing with the operation of the above-described channel switchover connection, switchover of the oscillation circuit 51 by the switch 52 serving as a load switchover unit is performed. That is, when the oscillation output unit 31 is connected to the measuring unit 200 by switchover of the switches SW1, SW5 and SW7 shown in FIG. 2 on the contact points A sides, the switch 52 in the oscillation output unit 31 switches over on the contact point A side, and the switches 52 in the oscillation output units 32 to 38, which are the other channels, switchover on the contact points B sides, so that the output side of these oscillation circuits 51 is connected to the terminal load 54. Thus, the switchover connection between the oscillation output unit 32 and the measuring unit 200, and the switchover connection of the load on the output side of the oscillation circuit 51 are conducted in synchronization with each other.

Figure 7:
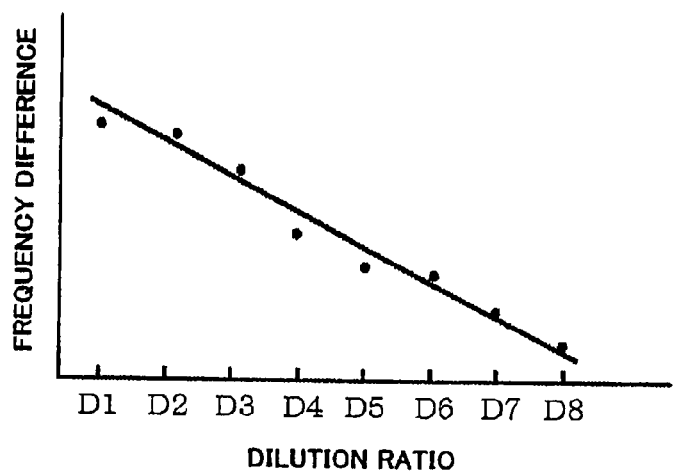
FIG. 7 is a characteristic diagram showing relation between deviation of respective frequency of 8 quartz sensors and dilution ratio of a sample solution in the above embodiment.

FIG. 7 shows relation between the dilution ratio of the sample solution and the deviation (difference in frequency) in frequency based on the measurement result measured for 8 channels as described above, and, for instance, evaluation of the concentration of the object in the sample solution is achieved based on this relation. It should be noted that the usage of the sensing device is not limited to the pouring sample solutions of which the original solutions are the same as each other and dilution ratios are varied, it is also applicable to the case when a sample solution differing the sample itself is poured into the quartz sensor.

According to the above embodiment, the common measuring unit 200 measures the variation in frequency and is provided to each oscillation circuit 51 corresponding to each quartz sensor 1 so as to switchover and connect in turn. As for the oscillation circuits 51 excepting the oscillation circuits 51 connected to the measuring unit 200 by the switches 52 serving as the load switchover unit, the load value on the output side of the oscillation circuit 51 included (relating to the measurement) in the channels connected to the measuring unit 200 and the load value on the output side of the standby oscillation circuit 51 are made different from each other, so that the respective oscillating frequencies are forcibly separated from each other. Therefore, the overlap of mutual spectrum can be avoided. Accordingly, the situation that the oscillation frequencies become unstable because the oscillation frequencies pull each other can be avoided, so that sensing of the object (measurement of concentration and detection of the presence or absence of the object) can be conducted in a stable fashion.

It should be noted that in this embodiment, the output sides of the oscillation circuits 51 are connected to the terminal loads 54 for all channels except the channel connected to the measuring unit 200. However, as for channels which are separated from the quartz sensor 1 relating to the measurement in some extent and have no chance of occurrence of spatial connection, they may be not connected on the terminal load 54 side and switchover control of the switch 52 may be conducted so as to connect on the terminal load 54 side, for only channels containing the quartz sensors 1 which are, for instance, adjacent to the quartz sensor 1 providing the measurement.

In the description above, it is possible that the measuring unit 200 measures as oscillation frequency in each quartz sensor 1 and counts, for instance, the blank value and the oscillation frequency when the sample solution is poured, and these count values are stored. Then, the difference between the two, in other words, the variation of the frequency is determined, or based on the variation, the concentration of an object to be detected is determined using a calibration curve obtained previously, and the concentration is displayed. Furthermore, a threshold value for the variation of the frequency is determined in advance, so that the presence or absence of an object is determined. The measuring unit 200 is not limited to that which counts the oscillation frequency of the oscillation circuit 51, but it may be are that directly determines the variation of the oscillation frequency.

As a method of directly determining the variation of an oscillation frequency, it is possible to cite the following example. An frequency signal from the oscillation circuit 51 is sampled by the reference clock signal, the sampled value is converted into a digital signal by an A/D converter, and orthogonal detection by the digital signal is conducted for the frequency signal corresponding to the digital signal. Then, the real number portion and the imaginary number portion are taken out when displaying the rotation vector rotating at the speed corresponding to the variation of the frequency in the frequency signal in complex notation, and at the same time, the deviation in frequency of frequency signal is determined based on each time series data of the real number portion and the imaginary number portion.

Figure 8:
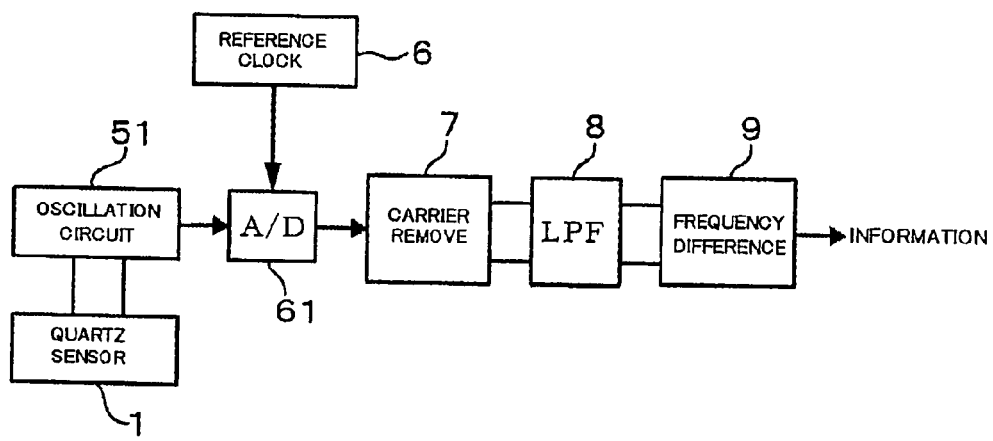
FIG. 8 is a characteristic diagram showing a situation in which a spectrum relating to the measurement overlaps with the other spectrum relating to the measurement between the quartz sensors adjacent to each other.

An example of carrying out the above-described method will be described. In FIG. 8, 6 is a reference clock generator and outputs a clock signal which is a frequency signal having an extremely high stability in frequency for the purpose of sampling a high frequency signal from the oscillation circuit 51, 61 is an A/D (analogue/digital) converter, which samples a high frequency signal from the oscillation circuit 51 by a clock signal from the reference clock generator 6 and outputs the sampling value thereof as a digital signal. The high frequency signal defined by this digital signal includes a harmonic as well as a fundamental wave. In other words, it is assumed that when a sine wave having harmonic distortion is sampled, the harmonic component is affected by turnaround, so that the fundamental frequency and the harmonic frequency sometimes overlap on the frequency axis in a frequency spectrum. Therefore, it is required to avoid such an overlap so as to obtain an accurate sensing operation.

In general, when a sine wave signal having a frequency of f1 is sampled by a clock signal having a frequency of fs, the frequency f2 as a result of the capturing is expressed by Equation (1), where mod (, ) indicates a modulo function.

$$f2 = |\mod(f1 + fs/2, fs) - fs/2| \ldots \quad (1)$$

In the result of this capturing, since the frequency of an n-power harmonic is expressed by n (frequency of fundamental) in regard to the fundamental, if this is put as f2 and substituted into the above Equation (1), it is possible to calculate the frequency of the captured harmonic. By using this calculation, it is possible to set the frequency fc of the high frequency signal from the oscillation circuit 51 and the sampling frequency (frequency of clock signal) fs so as not to overlap the frequency of the fundamental and that of the harmonic. For instance, fc is set to be 11 MHz, fs is 12 MHz. In this case, the fundamental of a frequency signal defined by the output signal which is a digital signal from the A/D converter 61 is a sine wave having a frequency of 1 MHz. Note that if fc/fs is set to be 11/12, though the frequency of the fundamental and the frequency of the harmonic do not overlap with each other, fc/fs is not limited to this value.

At the rear part of the A/D converter 61, a carrier remover 7 and a lowpass filter 8 are arrange din this order. The carrier remover 7 and the lowpass filter 8 correspond to a means for capturing a rotation vector relating to the variation in frequency of the sine wave signal. In more detail, a means is provided for capturing the real number portion and the imaginary portion when the rotation vector is displayed in complex notation, when the sine wave signal having a frequency of 1 MHz defined by a digital signal from the A/D converter 61 is A cos ($\omega_0 t + \theta$).

Figure 9:
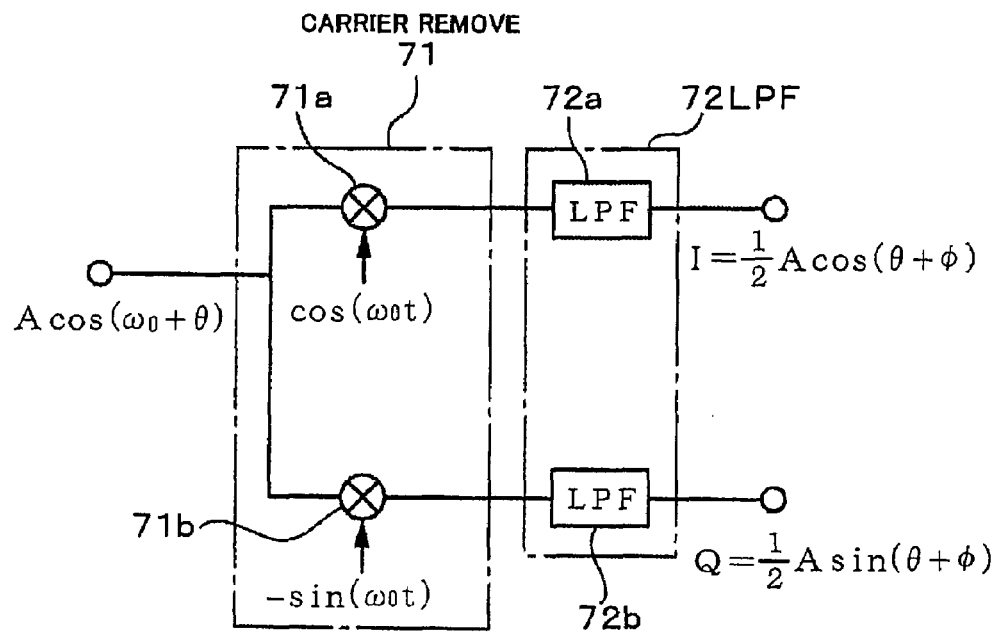
FIG. 9 is a structural diagram showing a portion of the circuit block shown in FIG. 8.

In other words, the carrier remove 7 includes a multiplier 71a multiplying cos ($\omega_0 t$) to the sine wave signal and a multiplier 71b multiplying –sin ($\omega_0 t$) to the sine wave signal as shown in FIG. 9. The output of the multiplier 71a and the output of the multiplier 71b are expressed by Equations (2) and (3) respectively.

$$A\cos(\omega_0 t+\theta)\cdot\cos(\omega_0 t)=\tfrac{1}{2}\cdot A\cos\theta+\tfrac{1}{2}\{\cos(2\omega_0 t)\cos\theta+\sin(2\omega_0 t)\cdot\sin\theta\}\ldots \quad (2)$$

$$A\cos(\omega_0 t+\theta)\cdot-\sin(\omega_0 t)=\tfrac{1}{2}\cdot A\sin\theta-\tfrac{1}{2}\{\sin(2\omega_0 t)\cdot\cos\theta+\cos(2\omega_0 t)\cdot\sin\theta\}\ldots \quad (3)$$

Accordingly, by letting the output of the multiplier 71a and the output of the multiplier 71b pass through the low pass filters 72a and 72b respectively, ½·A cos 0 and ½·A sin 0 are captured from the low pass filter 72, because the frequency signal $2\omega_0 t$ is removed. Note that the low pass filter 72 is described as to be composed of low pass filters 72a and 72b. Actual digital processing in the low pass filter 72 calculates the moving average of successive plural data, for instance 6 pieces of data, among the time series data outputted from the carrier remove 71.

When the frequency of a sine wave signal expressed by $A\cos(\omega_0 t+\theta)$ is varied, $A\cos(\omega_0 t+\theta)$ becomes $A\cos(\omega_0 t+\theta+\omega_1 t)$. Accordingly, ½·A cos θ becomes ½·A cos $(\theta+\omega_1 t)$, and ½·A sin θ becomes ½·A sin $(\theta+\omega_1 t)$. In other words, the output obtained from the low pass filter 72 is the signal corresponding to the variation of a frequency ($\omega_1 t$) of the sine wave signal [$A\cos(\omega_0 t+\theta)$], in more detail, the real number portion (T) and the imaginary number portion (Q) when a vector rotating at a speed of the variation in frequency is displayed in complex notation.

Figure 10:
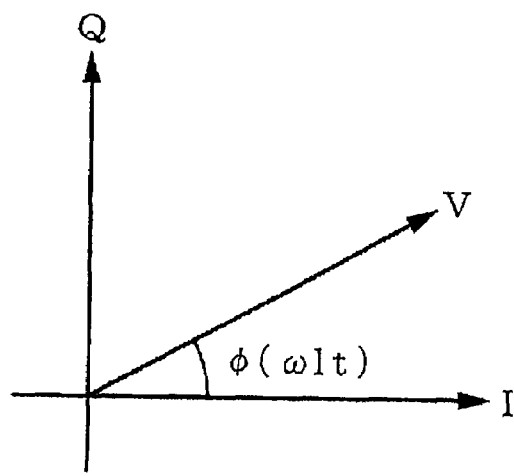
FIG. 10 is an explanatory diagram showing a rotation vector taken from the block diagram shown in FIG. 8.
Figure 11:
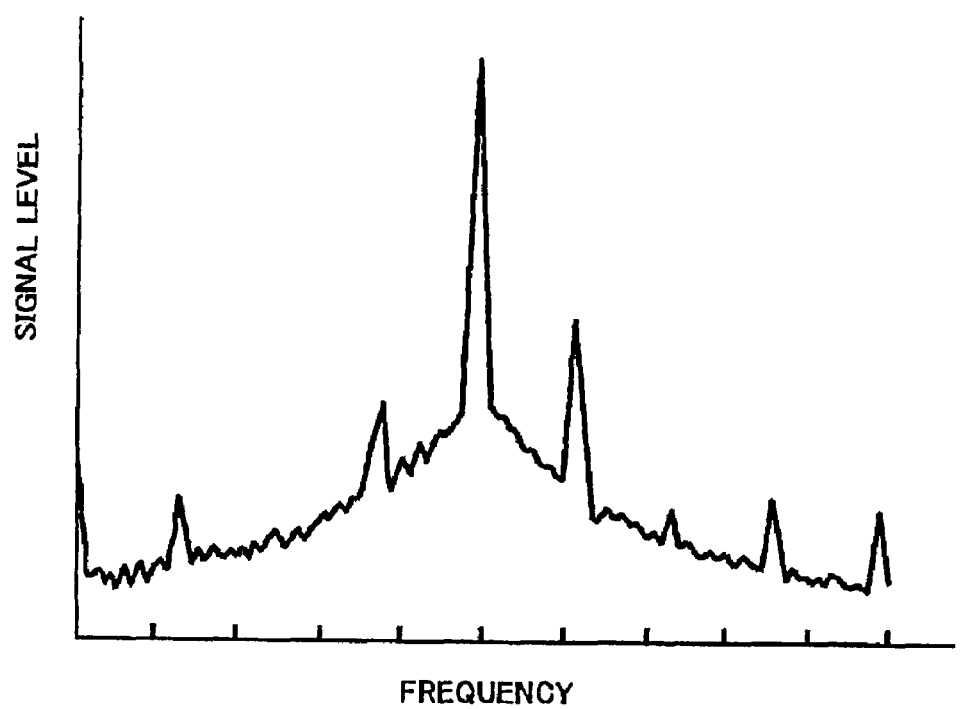
FIG. 11 is a block diagram showing an application example of the present invention.

FIG. 10 is a drawing indicating the rotation vector. The rotation vector is A in length, and $\omega_1 t$ in rotational speed. Accordingly, if the frequency of the sine wave signal is not varied, the rotational speed of the rotation vector is zero, because $\omega_1 t$ is zero. However, when an object is adsorbed on the quartz resonator 24, the frequency of the quartz resonator 24 varies, which varies the frequency of the sine wave signal, it rotates at a rotational speed in response to the variation. Accordingly, it is possible to obtain the frequency difference, in other words, the variation in frequency by computing the speed at a frequency difference calculator 9 based on the real number portion (I) and the imaginary portion (Q) at the time of displaying in complex notation of the rotation vector outputted form the low pass filter 72. It should be noted that a method of determining the phase of a rotation vector at a timing and the phase of the rotation vector at the timing determined by the next clock so that the phase difference between both phases is determined is adoptable for this computation.

The invention claimed is:

1. A sensing device for sensing objects in a medium, comprising:
    resonator elements each having an adsorbing surface configured to adsorb an object to be measured from said medium, and a natural frequency determined by absence or presence of an object adsorbed on said adsorbing surface;
    oscillation circuits, each of said oscillation circuits having an oscillation output, and an input connected to a respective one of said resonator elements so as to produce an oscillation signal having an oscillation frequency determined at least in part by said natural frequency of said connected one of said resonator elements and loading at said oscillation output;
    a measuring unit having a signal measurement input and a measurement output, said measuring unit being configured to measure an oscillation frequency of an oscillation signal of said oscillation signals applied to said signal measurement input;
    a signal switching unit connected to said oscillation circuits, said signal switching unit being configured to selectively connect said oscillation outputs to said measuring unit such that individual ones of said oscillation signals produced by said oscillation circuits are successively applied to said signal measurement input;
    load switching units and terminals loads, each of said oscillation circuits having said oscillation output connected to a respective one of said load switching units, said load switching units being configured to selectively connect said oscillation output to a respective one of said terminal loads;
    said terminal loads having a sufficient loading value such that, when applied to said oscillation outputs of said oscillation circuits by said load switching units, said terminal loads shift said oscillation frequencies an amount sufficient to prevent spectrum overlap with said oscillation frequencies of other ones of said oscillation circuits without said terminal loads applied to said oscillation outputs; and
    a switching controller configured to control said signal switching unit and said load switching units such that:
        said signal switching unit successively connects said oscillation outputs one output at a time to said measuring unit to effect one connection at a time;
        said load switching units do not apply an associated one of said terminal loads to said one output of said oscillation outputs when said one output of said oscillation outputs is connected to said measuring unit; and
        said load switching units apply an associated one of said terminal loads to at least one of said oscillation outputs when said at least one of said oscillation outputs is not connected to said measuring unit.

2. The sensing device of claim 1 further comprising a buffer circuit arrangement for completing said one connection at a time between said one output of said oscillation outputs to said measuring unit.

3. The sensing device of claim 2 wherein said buffer circuit arrangement include buffer circuits each associated with one of said oscillation circuits for completing said one connection at a time between said one output of said oscillation outputs to said measuring unit, said buffer circuits being disposed between said load switching units and said signal switching unit.

4. The sensing device of claim 3 wherein said load switching units are disposed between said oscillation circuits and said buffer circuits.

5. The sensing device of claim 1 wherein said buffer circuit arrangement includes buffer circuits each associated with one of said oscillation circuits for completing said one connection at a time between said one output of said oscillation outputs to said measuring unit, said load switching units being disposed between said oscillation circuits and said buffer circuits.

6. The sensing device of claim 1 wherein said at least one of said oscillation outputs having said terminal load applied thereto at a time when not connected to said measuring unit includes all of said oscillation outputs which are not connected to said measuring unit.

7. The sensing device of claim 1 further comprising:
    sensor housings, each housing a respective one of said resonator elements so as to provide a communication route to apply said medium to said resonator element, and each including terminals providing electrical connection to said resonator element; and
    a measuring device main unit including said oscillation circuits and connection devices detachably connecting said terminals of said sensor housings to respective ones of said oscillation circuits.

8. The sensing device of claim 7 further comprising a buffer circuit arrangement for completing said one connection at a time between said one output of said oscillation outputs to said measuring unit.

9. The sensing device of claim 8 wherein said buffer circuit arrangement include buffer circuits each associated with one of said oscillation circuits for completing said one connection at a time between said one output of said oscillation outputs to said measuring unit, said buffer circuits being disposed between said load switching units and said signal switching unit.

10. The sensing device of claim 9 wherein said load switching units are disposed between said oscillation circuits and said buffer circuits.

11. The sensing device of claim 8 wherein said buffer circuit arrangement includes buffer circuits each associated with one of said oscillation circuits for completing said one connection at a time between said one output of said oscillation outputs to said measuring unit, said load switching units being disposed between said oscillation circuits and said buffer circuits.

12. The sensing device of claim 7 wherein said at least one of said oscillation outputs having said terminal load applied thereto at a time when not connected to said measuring unit includes all said oscillation outputs not connected to said measuring unit.

13. A sensing device for sensing objects in a medium, comprising:
    resonator elements each having an adsorbing surface configured to adsorb an object to be measured from said medium, and a natural frequency determined by absence or presence of an object adsorbed on said adsorbing surface;
    oscillation circuits, each of said oscillation circuits having an output, and an input connected to a respective one of said resonator elements so as to produce an oscillation signal having an oscillation frequency determined at least in part by said natural frequency of said connected one of said resonator elements and loading at said oscillation output;
    a measuring unit having a signal measurement input and a measurement output, said measuring unit being configured to measure an oscillation frequency of an oscillation signal of said oscillation signals applied to said signal measurement input;
    a signal switching unit connected to said oscillation circuits, said signal switching unit being configured to selectively connect said oscillation outputs of said oscillation circuits to said measuring unit such that individual ones of said oscillation signals produced by said oscillation circuits are successively applied to said signal measurement input;
    terminal loads configured to communicate a signal to ground;
    load switching units provided between said oscillation circuits and said measuring unit along with associated ones of said terminal loads, each of said oscillation circuits having said oscillation output connected to a respective one of said load switching units, said load switching units each being configured to selectively connect said oscillation output of a corresponding one of said oscillation circuits alternately to:
        a first contact selectively connected to said measuring unit by said signal switching unit; and
        a second contact connected to ground by a respective one of said terminal loads;
    said terminal loads having a sufficient loading value such that, when applied to said oscillation outputs by said load switching units, said terminal loads shift said oscillation frequencies an amount sufficient to prevent spectrum overlap with said oscillation frequencies of other ones of said oscillation circuits without said terminal loads applied to said oscillation outputs; and
    a switching controller configured to control said signal switching unit and said load switching units to successively connect individual ones of said oscillation circuits to said measuring input one connection at a time, said switching controller effecting said control such that:
        said signal switching unit successively connects individual ones of said first contacts of the load switching units to said signal measurement input, and the load switching units concurrently provides connection between said oscillation outputs of said individual ones of said oscillation circuits and the successively connected individual ones of the first contacts; and
        said load switching units not having said successively connected individual ones of the first contacts, each connect said oscillation outputs associated therewith to corresponding ones of said second contacts to apply said terminal loads connected to said second contacts to said oscillation outputs such that all of said oscillation outputs not connected to said signal measurement input are connected to said terminal loads.

14. The sensing device of claim 13 further comprising:
    sensor housings, each housing a respective one of said resonator elements so as to provide a communication route to apply said medium to said resonator element, and each including terminals providing electrical connection to said resonator element; and
    a measuring device main unit including said oscillation circuits and connection devices detachably connecting said terminals of said sensor housings to respective ones of said oscillation circuits.

15. The sensing device of claim 13 further comprising a buffer circuit arrangement for completing said one connection at a time between said one output of said oscillation outputs to said measuring unit.

16. The sensing device of claim 15 wherein said buffer circuit arrangement include buffer circuits each associated with one of said oscillation circuits for completing said one connection at a time between said one output of said oscillation outputs to said measuring unit, said buffer circuits being disposed between said load switching units and said signal switching unit.

17. The sensing device of claim 16 wherein said load switching units are disposed between said oscillation circuits and said buffer circuits.

18. The sensing device of claim 15 wherein said buffer circuit arrangement includes buffer circuits each associated with one of said oscillation circuits for completing said one connection at a time between said one output of said oscillation outputs to said measuring unit, said load switching units being disposed between said oscillation circuits and said buffer circuits.

* * * * *